United States Patent [19]
Jensenius et al.

[11] Patent Number: 5,338,661
[45] Date of Patent: Aug. 16, 1994

[54] MONOCLONAL ANTIBODY SPECIFIC FOR A HUMAN TUMOUR-ASSOCIATED ANTIGEN

[76] Inventors: Jens C. Jensenius, Finsens Allé 28, 5230 Odense M; Per Borup-Christensen, Christian Lundsvej 1, 5792 Årslev; Karin Erb, Belvedere 11, 5700 Svendborg, all of Denmark

[21] Appl. No.: 411,469
[22] PCT Filed: Mar. 30, 1988
[86] PCT No.: PCT/DK88/00059
 § 371 Date: Sep. 29, 1989
 § 102(e) Date: Sep. 29, 1989
[87] PCT Pub. No.: WO88/07377
 PCT Pub. Date: Oct. 6, 1988

[30] Foreign Application Priority Data
 Apr. 3, 1987 [DK] Denmark ............... 1699/87

[51] Int. Cl.$^5$ ............... G01N 33/574; G01N 33/546; C07K 15/14
[52] U.S. Cl. ............... 435/7.23; 436/63; 436/64; 436/813; 436/512; 436/533; 436/534; 530/387.7; 530/388.15; 530/388.8; 530/388.85; 530/389.7
[58] Field of Search ............... 435/7.23, 172.2; 436/63, 64, 547, 548, 813, 512, 533, 534; 530/387, 387.7, 388.15, 388.8, 388.85, 389.7; 935/110

[56] References Cited

FOREIGN PATENT DOCUMENTS

| | | |
|---|---|---|
| 0066786 | 12/1982 | European Pat. Off. . |
| 119556 | 9/1984 | European Pat. Off. . |
| 151030 | 8/1985 | European Pat. Off. . |
| 154550 | 9/1985 | European Pat. Off. . |
| 0178891 | 4/1986 | European Pat. Off. . |
| 0200464 | 5/1986 | European Pat. Off. . |
| 199586 | 10/1986 | European Pat. Off. . |
| 0242154 | 10/1987 | European Pat. Off. . |

OTHER PUBLICATIONS

Girardet, et al.; J. of Immunology; 136(4):1497-1503 (1986); Immunochemical Characterization of Two Antigens Recognized by New Monoclonal Antibodies Against Human Colon Carcinoma.

Herlyn, et al.; PNAS; 76(3):1438-1442 (1979); Colorectal Carcinoma-Specific Antigen: Detection by Means of Monoclonal Antibodies.

Herlyn, et al.; Cancer; 27:769-774 (1981); Monoclonal Anticolon Carcinoma Antibodies in Complement-Dependent Cytotoxicity.

Brown, et al.; Bioscience Reports; 3:163-170 (1983); A Monoclonal Antibody Against Human Colonic Adenoma Recognizes Difucosylated Type-2-Blood-Group Chains.

Thompson, et al.; Cancer; 47:595-605 (1983); Monoclonal Antibodies to Human Colon and Colorectal Carcinoma.

Kaszubowski, et al.; Cancer Res.; 44:1194-1199 (1984); A Cytotoxic Monoclonal Antibody to Colon Adenocarcinoma.

Morgan, et al.; Hybridoma; 3(3):233-245 (1984); Monoclonal Antibodies to Human Colorectal Tumor-Associated Antigens: Improved Elicitation and Subclass Restriction.

Drewinko, et al.; Cancer Res.; 46:5137-5143 (1986); New Monoclonal Antibodies against Colon Cancer-Associated Antigens.

Gazdar, et al.; Cancer Res.; 41:2773-2777 (1981); Levels of Creatine Kinase and Its BB Isoenzyme in Lung Cancer Specimens and Cultures.

Syamal Raychaudhuri, Yukihiko Saeki, Hiroshi Fuji and Heinz Kohler "Tumor-Specific Idiotype Vaccines", vol. 137, pp. 1743-1749, No. 5 "The Journal of Immunology".

Alfred Nisonoff, John E. Hopper and Susan B. Spring, "The Antibody Molecule".

Ronald C. Kennedy, Joseph I. Mednick and Gordon R. Dreesman, "Anti-Iodiotypes and Immunity".

*Primary Examiner*—Toni R. Scheiner
*Attorney, Agent, or Firm*—Iver P. Cooper

[57] ABSTRACT

The present invention provides a human monoclonal antibody (C-OU1) which specifically binds a human adenocarcinoma tumor-associated antigen with an apparent molecular weight of about 43 kD and an isoelectric point of about 5.4–6.2. Screening assays using the antibody are also disclosed.

13 Claims, 6 Drawing Sheets

000
MONOCLONAL ANTIBODY SPECIFIC FOR A HUMAN TUMOUR-ASSOCIATED ANTIGEN

FIELD OF INVENTION

The present invention relates to a tumour-associated antigen, an antibody directed against the antigen, a diagnostic agent comprising the antigen or the antibody, a pharmaceutical composition comprising the antigen or the antibody, and the use of the antigen or the antibody for a variety of diagnostic or therapeutic purposes.

BACKGROUND OF THE INVENTION

The possibility of developing more precise methods of detecting and diagnosing cancer by identifying and characterizing tumour-associated antigens (i.e. antigens expressed by tumours) is of great medical interest.

Monoclonal antibodies against tumour-associated antigens may play an important role for the detection of cancer because of their greater specificity. To date most of the monoclonal antibodies raised against cancer-associated antigens have been of mouse origin, being expressed by hybridomas resulting from a fusion of spleen cells from a mouse immunized with a human cancer cell line or cells from a cancer patient with a mouse myeloma cell line. Immunogenicity in the mouse is a requirement for antigens recognized by murine monoclonal antibodies and they do not necessarily correspond to antigens recognized by human antibodies. In addition, the therapeutic value of these murine monoclonal antibodies may be limited since patients recognize these antibodies as foreign proteins and may therefore develop an adverse immune response against the murine antibody. The result may be a neutralization of the therapeutic effect and triggering of potentially dangerous allergic reactions.

Human hybridoma antibodies may be more promising as diagnostic and therapeutic agents for administration to patients with cancer under the assumption that human monoclonal antibodies are less immunogenic in humans than heterologous antibodies and are capable of recognizing the relevant antigens.

Problems related to the specificity of murine monoclonal anti-tumour antibodies are illustrated by the colon adenocarcinoma antibody 17-A1, which has been used in diagnosis and therapy, but has now been found to react with normal as well as tumour tissue (*Hybridoma* 5 Suppl. 1, 1986, special issue on Ca-17-A1, ed. Z. Steplewski).

The immune response in patients against administered murine monoclonal antibody has been described by numerous investigators (e.g. H. F. Sears et al., Lancet 1985, i:762-765; and M. S. Mitchell et al., *Prog. Cancer Res. Ther.* 21, 1982, Raven Press, New York).

Colo-rectal cancer is one of the most frequently occurring cancers and one of the major causes of death from cancer. The prognosis of this cancer type has not improved for a long period of time, and novel methods for the detection of colo-rectal cancer and adjuvant therapy concomitantly with surgery thereof are therefore needed.

Therefore, a need exists for a human carcinoma tumour-associated antigen, in particular one which is substantially not expressed by normal tissue, and antibodies against such an antigen for diagnostic and therapeutic purposes.

DESCRIPTION OF THE INVENTION

Accordingly, the present invention relates to a human carcinoma-associated antigen which has an apparent molecular weight of about 43,000 and an isoelectric point in the range of about 5.4–6.2, and which has at least one epitope which is reactive with a monoclonal antibody produced by the human hybridoma cell line B9165 (ECACC 87040201), or an analogue thereof.

The term "analogue" is used in the present context to indicate a protein or polypeptide of a similar amino acid composition or sequence as the present antigen, allowing for minor variations which do not have an adverse effect on the immunogenicity of the analogue. The analogous polypeptide or protein may be derived from another source than carcinoma tissue such as from a recombinant organism or may be partially or completely of synthetic origin. The term is further intended to mean any derivative of The antigen such as an immunogenic subsequence thereof.

Immunocytochemical analysis by standard procedures using a monoclonal antibody with specific reactivity to the antigen indicates the presence of the novel antigen in human colon carcinoma and mammary carcinoma tissue, but not in duodenal adenocarcinoma tissue, melanoma or Burkitt's lymphoma tissue or human peripheral blood leukocytes (cf. Table I below).

Immunohistochemical analysis by standard procedures using a monoclonal antibody with specific reactivity to the antigen indicates the presence of the novel antigen in colon adenocarcinoma, ovarian adenocarcinoma, renal adenocarcinoma, mammary adenocarcinoma, lung adenocarcinoma and non-seminomal testis carcinoma tissues, but not in lung epithelial carcinoma, sarcoma, malignant melanoma, B-lymphoma or thymoma tissue or in normal tissues except for mammary tubules, mammary ductuli or prostate epithelium (cf. Tables IIA and IIB below).

It is therefore concluded that the novel antigen is one which is substantially not found in normal human tissue and which has been found to be expressed by carcinoma tissue, in particular adenocarcinoma tissue, but not by other malignant tissues as determined by standard immunocytochemical and immunohistochemical analyses. In particular, the novel antigen seems to be one associated with colon adenocarcinoma.

A tumour-associated antigen expressed by colon carcinoma is disclosed in EP 199 586. This antigen, however, differs from the antigen of the present invention in characteristics such as molecular weight and isoelectric point, and it is indicated to be present in both normal and malignant colon tissue (i.e. it does not appear to be tumour-specific) wherease the antigen of the present invention has been shown to be present in several different malignant tissues, as indicated above.

The antigen of the invention may for instance be obtained by isolation from extracts of carcinoma cells or extracts of carcinoma tumours by affinity chromatography on an insolubilized antibody raised against the antigen according to procedures known to those skilled in the art (cf. Johnstone, A. & Thorpe, R., *Immunochemistry in Practice,* Blackwell, Oxford 1987). Further purification by one or more additional protein purification procedures (e.g. size exclusion chromatography, ion exchange chromatography, ligand affinity chromatography, hydrophobic interaction chromatography, electrophoresis in gels with or without denaturation, and various precipitation procedures) may be necessary to obtain the antigan in sufficiently pure form for detailed molecular characterization and for use for diagnostic or therapeutic purposes.

In order to ensure an adequate supply of the antigen, it may, however, be advantageous to produce the antigan by recombinant DNA techniques. These may comprise (a) isolating a nucleotide sequence coding for the antigen, e.g. by establishing a cDNA or gene library of human carcinoma cells and screening for positive clones in accordance with conventional methods; (b) inserting said sequence in a suitable, replicatable expression vector; (c) transforming a suitable host microorganism with the vector produced in step (b); (d) cultivating the microorganism produced in step (c) under suitable conditions for expressing the antigen; and (e) harvesting the antigen from the culture.

Steps (a)–(e) of the process may be carried our by standard methods, e.g. as described in Maniatis et al., *Molecular Cloning: A Laboratory Manual*, Cold Spring Harbor, 1982.

Once the gene coding for the antigan has been isolated, it may be possible to establish the DNA sequence by standard procedures, e.g. as described by Sanger et al., *Science* 214, 1981, p. 1205, or Gilbert, *Science* 214, 1981, p. 1305, and the amino acid sequence may be deduced on the basis of the DNA sequence. The antigan or a subsequence thereof may then be produced by conventional peptide synthesis, e.g. liquid or solid phase peptide synthesis, solid phase peptide synthesis being the preferred procedure (cf. R. B. Merryfield, *J. Am. Chem. Soc.* 85, 1963, p. 2149, or Stewart and Young, *Solid Phase Peptide Synthesis*, Freeman & Co., San Francisco, USA, 1969). In solid phase synthesis, the amino acid sequence is constructed by coupling an initial amino acid to a solid support and then sequentially adding the other amino acids in the sequence by peptide bonding until the desired length has been obtained.

In another aspect, the present invention relates to an antibody which is specifically directed against the carcinoma antigen described above.

The antibody is advantageously a monoclonal antibody since these tend to be of a higher specificity than polyclonal antibodies, making them useful for accurate diagnostic determinations. Due to the considerations outlined above, the antibody when intended for injection into patients should preferably be of human origin, that is, be one produced by a fusion product of a human lymphocyte and a human cell line or a fusion product of a human lymphocyte and, for instance, a murine myeloma cell line, rather than a fusion product of a murine lymphocyte and a murine myeloma cell line, which has hitherto been usual for the production of monoclonal antibodies against human tumour-associated antigens. Such monoclonal antibodies may be raised against different epitopes on the antigen. One example of a useful monoclonal antibody is the one denoted C-OU1 produced by the human hybridoma cell line B9165 which was deposited on Apr. 2, 1987, in the European Collection of Animal Cell Cultures (ECACC), Centre for Applied Microbiology and Research, Porton Down, Salisbury, Wiltshire, Great Britain, with the accession number ECACC 87040201.

The monoclonal antibody of the invention may be-prepared by a method comprising
a) isolating antibody-producing cells from a cancer patient,
b) fusing cells producing the antibody with cells of a suitable human fusion cell line, and selecting and cloning the resulting hybridoma cells producing said antibody, and
c) growing the cells of step b) in a suitable medium to produce said antibody, and harvesting the antibody from the growth medium.

The antibody-producing cells used for fusion to the human fusion cells are preferably spleen or lymph node cells. The fusion of anti-body-producing cells and human fusion cells may be performed substantially as described by Köhler and Milstein, *Nature* 256, 1975, p. 495, or Köhler, *Immunoligical Methods* Vol. II, Academic Press, 1981, pp. 285–298, that is, preferably in the presence of a fusion promoter such as polyethylene glycol. The human fusion cell line employed is preferably of a type unable to survive in selective medium; one type of cell line frequently used for cell fusions is one which lacks the enzyme hypoxanthine-guanine phosphoribosyltransferase and which is consequently unable to grow in a medium containing hypoxanthine, aminopterin and thymidine (HAT medium).

The selection of hybridoma cells which produce an antibody against the carcinoma antigen may then be carried out by culturing unfused antibody-producing cells, unfused human fusion cells and supposedly fused cells in a selective medium (such as HAT) in which the unfused human fusion cells cannot grow and eventually die out. The unfused antibody-producing cells can only survive for a limited period of time after which they also die out. On the other hand, successfully fused cells continue to grow as they have inherited permanent growth properties from the parent human fusion cells and the ability to survive in the selective medium from the parent antibody-producing cells.

The resulting antibody-producing cells may be grown in vitro after cloning in a suitable medium, such as RPMI 1640. This results in the production of monoclonal antibodies of a very high purity as these are secreted into the culture supernatant by the cells. The antibodies may then be isolated by conventional methods such as centrifugation, filtration, precipitation, chromatography, or a combination thereof.

For purposes not requiring monoclonality, the antibody may be a polyclonal antibody. This may be prepared by injecting a suitable animal (e.g. a rabbit, mouse or goat) with a substantially pure preparation of the antigen followed by one or more booster injections at suitable intervals (e.g. two weeks to a month) up to six months before the first bleeding. Then, while continuing this established immunization regimen, the animals are bled about one week after each booster immunization, and antibody is isolated from the serum in a conventional manner, e.g. as described in Harboe and Ingild, *Scand. J. Immun.* 2 (Suppl. 1), 1973, pp. 161–164.

For some purposes, it may be an advantage that the antibody is a hybrid antibody which contains a combining site directed specifically against an epitope of the antigen of the invention and another directed specifically against another epitope of the same antigen, an epitope of another antigen or a pharmaceutical. The term "combining site" is understood to mean the antigen recognition structure in the variable region of the antibody molecule. Hybrid antibodies make special procedures possible for,detecting the antigen in a sample and for targeting a pharmaceutical or other biologically active molecule or another antigen to the site of the tumour where the reagent has the greatest effect. In an advantageous embodiment, the other antigen with which the hybrid antibody is reactive is a differentiation antigen of cytotoxic T-cells (cf. Staerz et al., *Nature* 314, 1985, p. 628). The pharmaceutical with which the hybrid antibody may be reactive is preferably selected from cytotoxic or antineoplastic agents (cf. Collier, R. J. and Kaplan, D. A., *Scientific American* 251, 1984, p. 44).

The hybrid antibody may be produced by hybrids between two monoclonal cell lines producing the two relevant antibodies or may be produced by chemically linking fragments of the two antibodies.

The antibody may, for different purposes, vide below, be an anti-idiotypic antibody, i.e. an antibody directed against the site of an antibody which is reactive with the epitope on the antigen. The anti-idiotypic antibody is directed against an antibody which is reactive with the antigen of the invention. The anti-idiotypic antibody may be prepared by a similar method to that outlined above for the monoclonal or polyclonal antibody. The antibody may also be an anti-anti-idiotypic antibody directed against the anti-idiotypic antibody defined above.

In a further important aspect, the present invention relates to a diagnostic agent which comprises an antibody of the invention as described above, an anti-idiotypic antibody as described above, or an anti-anti-idiotypic antibody as described above.

Although in some cases, such as when the diagnostic agent is to be employed in an agglutination assay in which solid particles to which the antibody is coupled agglutinate in the presence of a carcinoma antigen in the sample subjected to testing, no labelling of the antibody is necessary, it is preferred for most purposes to provide the antibody with a label in order to detect bound antibody. In a double antibody ("sandwich") assay, at least one of the antibodies may be provided with a label. Substances useful as labels in the present context may be selected from enzymes, fluorescent substances, radioactive isotopes and ligands such as biotin.

Examples of enzymes which may be used as label substances are peroxidases, e.g. horseradish peroxidase, or phosphatases, e.g. alkaline phosphatases. As enzymes are not directly detectable, they must be combined with a substrate to form a detectable reaction product which may, for instance, be fluorescent or coloured. Examples of useful substrates are $H_2O_2$/o-phenylene diamine, $H_2O_2$/azinodiethylbenzthiazoline sulphonic acid, $H_2O_2$/diaminobenzidine and p-nitrophenylphosphate. Such reaction products may be detected by the naked eye as a colour emergence or change, or by means of a spectrophotometer.

Examples of fluorescent substances useful as label substances are $H_2O_2$/p-hydroxyphenylacetic acid and methylumbelliferyl phosphate. Such substances may be detected by means of a fluorescence spectrophotometer in a manner known per se.

Examples of radioactive isotopes useful as label substances are I-125, S-35 and P-35. The radioactivity emitted by these isotopes may be measured in a gamma-counter or a scintillation counter in a manner known per se.

In a favoured embodiment, the diagnostic agent comprises at least one antibody coupled to a solid support. This may be used in a double antibody assay in which case the antibody bound to the solid support is not labelled while the unbound antibody is labelled. The solid support may be composed of a polymer or may comprise a matrix on which the polymer is applied. The solid support may be selected from a plastic, e.g. latex, polystyrene, polyvinylchloride, nylon, polyvinylidene difluoride, or cellulose, e.g. nitrocellulose, silicone, silica and a polysaccharide such as agarose or dextran.

For use in a diagnostic assay, the solid support may have any convenient shape. Thus, it may be in the form of a plate, e.g. a thin layer or, preferably, microtiter plate, a strip, film, paper or microparticles such as latex beads or the like.

Rather than being coupled directly to the solid support, the monoclonal antibody may be coupled to a spacer immobilized on a solid support. Examples of spacers include Protein A.

It should be noted that practically all methods or applications based on intact antibodies could instead be performed using fragments of the antibodies, e.g. F(ab')$_2$ or Fab fragments (cf. Delaloye, B. et al., *J. Clin. Invest.* 87, 1986, p. 301).

For use in a sandwich assay, the diagnostic agent may additionally comprise another antibody. This other antibody may be labelled and/or coupled to a solid support as described above. In this embodiment, either or both of the antibodies may be a monoclonal antibody as described above.

Alternatively, the diagnostic agent of the invention may comprise a carcinoma antigen as defined above. This agent may be used to detect the presence of antibodies against the carcinoma antigen in a sample. The diagnostic agent may otherwise exhibit any of the features described above for diagnostic agents comprising an antibody of the invention, although they will detect bound antibody rather than binding of an antibody to the antigen.

In a still further aspect, the invention relates to a method of in vitro diagnosing human carcinoma expressing the antigen of the invention, comprising contacting a sample of a body fluid from a suspected cancer patient with a diagnostic agent according to the invention comprising an antibody of the invention, and determining the presence of bound antigen. The antibody may be labelled and/or bound to a solid support as exemplified above. The body fluid may be selected from blood, plasma, serum, lymph, lung expectorate, urine and gastrointestinal fluids.

In a favoured embodiment of the method, the sample is incubated with a first monoclonal antibody coupled to a solid support and subsequently with a second monoclonal or polyclonal antibody provided with a label. An example of this embodiment is the sandwich ELISA (enzyme linked immuno sorbent assay) described in Voller, A. et al., *Bull. World Health Organ.* 53, 1976, p. 55.

In an alternative embodiment (a so-called competitive binding assay), the sample may be incubated with a monoclonal antibody coupled to a solid support and subsequently with a labelled carcinoma antigen, the latter competing for binding sites on the antibody with any carcinoma antigen present in the sample.

An alternative embodiment relates to a method of in vitro diagnosing human carcinoma expressing the antigen of the invention, comprising contacting a tissue sample from a suspected cancer patient with a diagnostic agent of the invention comprising an antibody of the invention, and determining the sites on the sample to which antibody is bound. Such an immunohistochemical method may be carried out according to well-established procedures, e.g. as described below in Example 2.

A further embodiment of a diagnostic method of the invention relates to a method of localizing tumours (in particular carcinomas) in vivo by means of the antibody of the invention. This method comprises administering a diagnostically effective amount of an antibody of the invention which is labelled so as to permit detection thereof, and determining the sites of localization of bound antibody. The antibody may be labelled by means of a radioactive isotope and subsequently injected and localized by known methods, e.g. a gamma ray detector of a suitable configuration (cf. Mach, J.-P. et al., Nature 248, 1974, p. 704).

A still further embodiment relates to a method of in vitro diagnosing human carcinoma expressing the antigen of the invention, comprising contacting a sample of a body fluid from a suspected cancer patient with a diagnostic agent of the invention comprising the antigen or the anti-idiotypic antibody of the invention, and determining the presence of bound antibody against the antigen of the invention present in said body fluid.

In yet another aspect, the invention relates to a pharmaceutical composition for the treatment of human carcinoma, which comprises an antigen according to the invention or an antibody according to the invention and a pharmaceutically acceptable excipient.

The excipient employed in the composition of the invention may be any pharmaceutically acceptable vehicle. This vehicle may be any vehicle usually employed in the preparation of injectable compositions, e.g. a diluent, suspending agent etc. such as isotonic or buffered saline. The composition may be prepared by mixing a therapeutically effective amount of the antigen or antibody with the vehicle in an amount resulting in the desired concentration of the antigen or antibody in the composition.

In some cases it may be advantageous to couple the antigen or antibody to a carrier, in particular a macromolecular carrier. The carrier is usually a polymer to which the toxin is bound by hydrophobic non-covalent interaction, such as a plastic, e.g. polystyrene, or a polymer to which the antigen or antibody is covalently bound, such as a polysaccharide, or a polypeptide, e.g. bovine serum albumin, oval-bumin or keyhole limpet hemocyanin. Furthermore, the carrier may advantageously be selected from a pharmaceutical, e.g. a cytotoxic or antineoplastic agent, to which the antigen or antibody is coupled. The carrier may also be another antibody directed against a cytotoxic effector mechanism, e.g. cytotoxic cells. The carrier should preferably be non-toxic and non-allergenic. The antigen or antibody may be multivalently coupled to the macromolecular carrier as this may provide an increased immunogenicity of the composition.

For oral administration, the composition may be in the form of a tablet, capsule, granulate, paste, gel, mixture or suspension optionally provided with a sustained-release coating or a coating which protects the antigen from passage through the stomach.

Solid formulations, i.e. granulates, tablets and capsules, may contain fillers, e.g. sugars, sorbitol, mannitol and silicic acid; binders, e.g. cellulose derivatives such as carboxymethyl cellulose and polyvinylpyrrolidone; disintegrants, e.g. starch, sodium bicarbonate and calcium carbonate; lubricants, e.g. magnesium stearate, talc and calcium stearate. Semisolid formulations, i.e. pastes or gels, may comprise a gelling agent such as an alginate, gelatin, carrageenan, tragacanth gum and pectin, a mineral oil such as liquid paraffin, a vegetable oil such as corn oil, sunflower oil, rape oil and grape kernel oil, as well as a thickener such as a starch, gum, gelatin, etc. Liquid formulations. i.e. mixtures and suspensions, may comprise an aqueous or oily vehicle, e.g. water, or a mineral oil such as liquid paraffin, a vegetable oil such as corn oil, sunflower oil, rape oil, grape kernel oil, etc. The antigen of the invention may be suspended in the liquid vehicle in accordance with usual practice.

The sustained-release coating may, e.g., be an enteric coating which may be selected from shellac, cellulose acetate esters such as cellulose acetate phthalate, hydroxypropylmethyl cellulose esters such as hydroxypropylmethyl cellulose phthalate, polyvinyl acetate esters such as polyvinyl acetate phthalate, and polymers of methacrylic acid and (meth)acrylic acid esters.

The composition may also be adapted for rectal administration, e.g. as a suppository. Such a suppository may contain conventional excipients such as cocoa butter or other glycerides.

Finally, the invention relates to the use of an antigen according to the invention or an anti-idiotypic antibody of the invention for preparing a medicament for the treatment of human adenocarcinoma, or to the use of an antibody or anti-anti-idiotypic antibody according to the invention and for preparing a medicament for the treatment of human carcinoma.

Therapy of cancers, in particular carcinomas, expressing the carcinoma antigen of the invention may be carried out by a variety of procedures known to those skilled in the art. An antibody against the antigen (in particular a human monoclonal antibody for the reasons stated above) may be injected into cancer patients to combat the tumour directly or via various effector mechanisms, e.g. complement-mediated cytotoxicity or antibody-dependent cell-mediated cytotoxicity. The antibody may be modified prior to injection into the patient as indicated above, e.g. by coupling to pharmaceuticals (thus transporting those to the site of their activity), or to another antibody directed against a cytotoxic effector mechanism such as antigens on cytotoxic T-cells or on other cytotoxic cells. It is contemplated that hybrid antibody containing one combining site for the antigen and another against another antigen or a pharmaceutical as described above may also advantageously be used to provide a two-way attack on the tumour in question.

The antibody of the invention may be used in extra-corporal devices for removing circulating tumour antigen or immune complexes containing tumour antigen, thereby reconstituting the anti-cancer immune response by allowing the immune system to recover from paralysis induced by said tumour antigen or immune complexes.

The carcinoma antigen of the invention may be used for immunization in order to provoke an anti-cancer immune response in the body. The antigen may further be used in vitro for raising effector cells against cancer by culturing the antigen with leukocytes from a cancer patient.

The carcinoma antigen may be used in extra-corporal devices for removing anti-tumour antibody or immune complexes in a similar way to that employing the antibody.

The antibody against the carcinoma antigen may furthermore be administered to provoke an anti-idiotypic or anti-anti-idiotypic immune response. An anti-idiotypic antibody (whether monoclonal or polyclonal or a fragment of these) raised against an antibody reacting with the carcinoma antigen of the invention may express epitopes similar to those of the antigen and may therefore be used in a similar fashion for immunization to raise an anti-carcinoma immune response. Such antibodies may further be used in extra-corporal devices as described above for the antigen and primary antibody.

Anti-anti-idiotypic antibodies may be used in ways similar to those described for primary anti-tumour antibodies.

BRIEF DESCRIPTION OF THE DRAWINGS

The invention will be described in further detail in the following Examples and with reference to the appended drawings, where.

EXAMPLE 1

Production Of human monoclonal antibody (C-OU1)

Figure 1A:
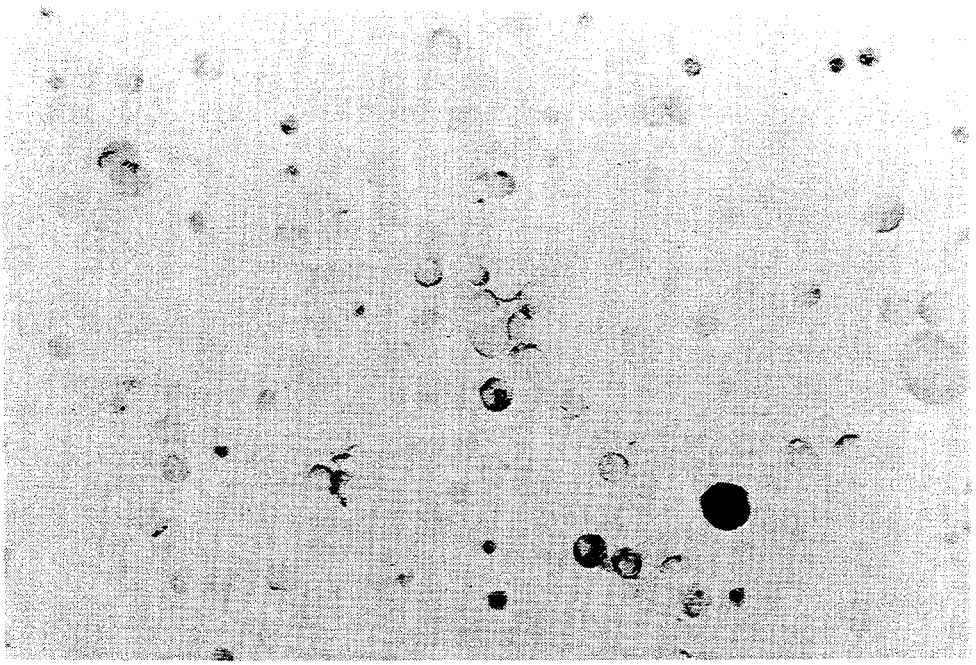
FIGS. 1A and 1B show immunocytochemical staining with C-OU1 of COLO 201 cells (colonic adenocarcinoma cells, positive) and staining of the same cells with a non-reacting human hybridoma IgM (negative)

Mesenteric lymph nodes draining the tumour region in patients with colo-rectal cancer were minced under sterile conditions. Debris were removed by filtration through cotton wool and the lymphocytes were purified by centrifugation on Ficoll-Isopaque (Boehringer-Mannheim, Mannheim, Federal Republic of Germany).

The lymphocytes were fused with the human fusion cell line W1-L2-729-HF2 (in the following referred to as HF2) (from Tecniclone Int., Santa Ana, Calif., USA) according to Köhler, *Immunological Methods* Vol. II, Academic Press, 1981, pp. 285-298. The ratio between the HF2 and lymphocytes ($10^7$) was 1:2.

After washing the HF2 and the lymphocytes together in RPMI-1640 medium followed by centrifugation, the cell pellet was resuspended in 0.5 ml of 50% PEG (polyethylene glycol) 6000 over a period of 1 minute with constant shaking. Before dilution of the PEG with RPMI-1640, the cells were incubated for another 2 minutes. Then the fusion product was washed and resuspended in solution medium [RPMI-1640, 10% FCS (fetal calf serum) supplemented with HAT ($2 \times 10^{-4}$M hypoxanthine, $4 \times 10^{-7}$M aminopterin, $3.2 \times 10^{-6}$M thymidine)]. The cells were plated at $2 \times 10^5$ cells in 200 µl per well of 96-well microtiter plates. The cells were maintained in selective medium for two weeks. Further culturing was carried out in RPMI-1640+10% FCS supplemented with hypoxanthine and thymidine. Growing hybrids appeared 10 days to 4 weeks after fusion. Cloning was performed by limiting dilution without feeder cells.

Supernatants from wells with growing clones were analyzed for immunoglobulin production by ELISA (enzyme linked immuno sorbent assay) on microtiter plates coated with rabbit anti-human Ig (H and L chain) (Dakopatts, Copenhagen, Denmark) diluted 1:10,000 in 0.1M bicarbonate, pH 9.6. Coated wells were washed with PBS-Tween (phosphate buffered saline—0.05% Tween 20) and incubated for 2 hours at room temperature with supernatants diluted 1:10 in PBS-Tween. Development was carried out with alkaline phosphatase (AP)-coupled antibody specific for IgM, IgA or IgG (Dakopatts, Copenhagen) diluted 1:3000 in PBS-Tween. After incubation for 1 hour at room temperature, the substrate p-nitrophenylphosphate (PNPP), 1 mg/ml 10% diethanolamine, 1 mM $MgCl_2$, pH 9.6, was added. Optical density was measured at 405 nm after 1 hour of incubation at 37° C. Standard curves for quantification were constructed with dilution of IgM (Cappel) or IgG (Kabi AB, Stockholm, Sweden). Hybrids producing immunoglobulin (Ig) assayed by ELISA were propagated by transfer to 24-well macroplates (Nunc A/S, Denmark), and the supernatants were further analyzed in immunocytochemical analysis for reaction with tumour cells or in immunohistochemical analysis for reactions with tumour tissues as described below.

The hybridoma cell line B9165 (ECACC 87040201) selected by the methods described below was shown by ELISA to produce between 1 and 5 µg of IgM per ml when allowed to grow for two weeks without any change of medium.

EXAMPLE 2

Antigen characterization a) Immunocytochemical analysis

The analysis for anti-tumour reactivity was carried out by immunocytochemical analysis and by immunohistochemical analysis. Immunocytochemical analysis was performed on cell smears prepared from different human tumour cell lines and peripheral human blood leukocytes. Cells were fixed on slides by treatment with formol-acetone (9.5% formaldehyde, 43% acetone in 86 mM phosphate buffer, pH 7.2). Approximately 50 µl of C-OU1 supernatant (from the hybridoma B9165; ECACC 87040201) was placed on the smear of fixed cells and incubated overnight at 4° C. in a humidified chamber before rinsing and incubation for 1 hour at room temperature with horseradish peroxidase (HRP)-labelled rabbit anti-human IgM (Dakopatts) diluted to 1:80 in PBS-Tween. Finally, peroxidase substrate (0.01% $H_2O_2$ and diaminobenzidine at 0.6 µg/ml in PBS) was added. The smears were lightly counterstained with hematoxylin and mounted. Table I shows the results obtained by analysis of C-OU1 on smears of various cells.

TABLE I

| Reactivity of C-OU1 assayed by immunocytochemistry | | |
|---|---|---|
| Type of cell | Name | Reaction |
| 1. Colon adenocarcinoma | Colon 137 | Positive |
| 2. Colon adenocarcinoma | COLO 201 | Positive |
| 3. Melanoma | HU 373 | Negative |
| 4. Mammary carcinoma | MCF-7 | Positive |
| 5. Duodenal adenocarcinoma | HUTU 80 | Negative |
| 6. Burkitt's lymphoma | EB-2 | Negative |
| 7. Human peripheral blood leukocytes | PBL | Negative |

Figure 1B:
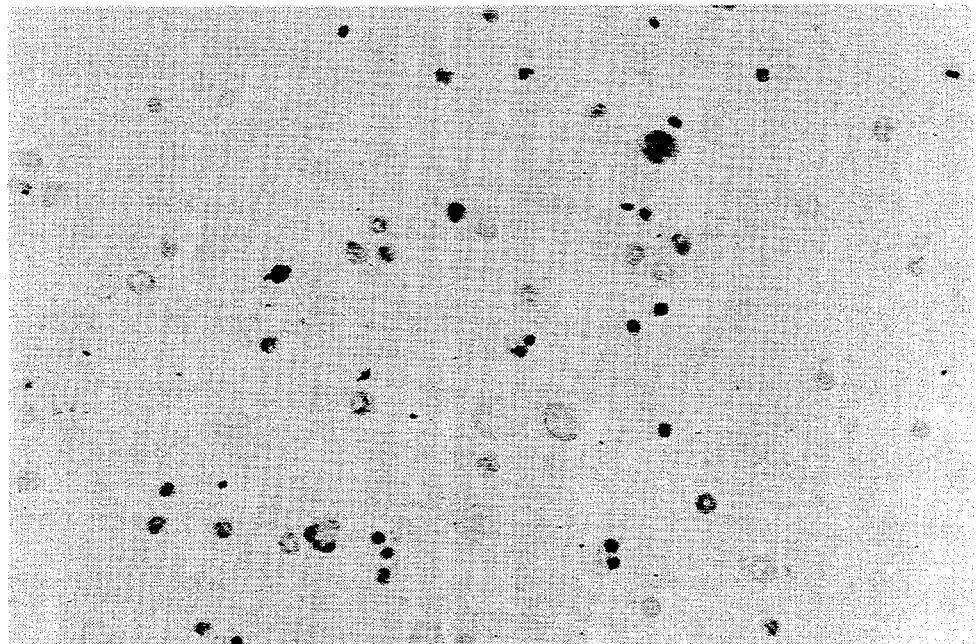

A selective reactivity is apparent. Alternatively, the live cells were incubated with the hybridoma antibody at 4° C., followed by the enzyme-labelled anti-Ig antibody. The cells were then smeared on slides, fixed with glutaraldehyde (0.17% in PBS) and incubated with substrate. FIG. 1A shows the staining of live COLO 201 cells (colonic adenocarctnoma cells) with C-OU1 while FIG. 1B shows the lack of staining when using a non-reactive human hybridoma IgM in the first layer. The method employed is the accepted standard procedure for labelling molecules exposed on the cell surface, and the labelling seen in FIG. 1 is in accordance with this.

b) Immunohistochemical analysis

Figure 2A:
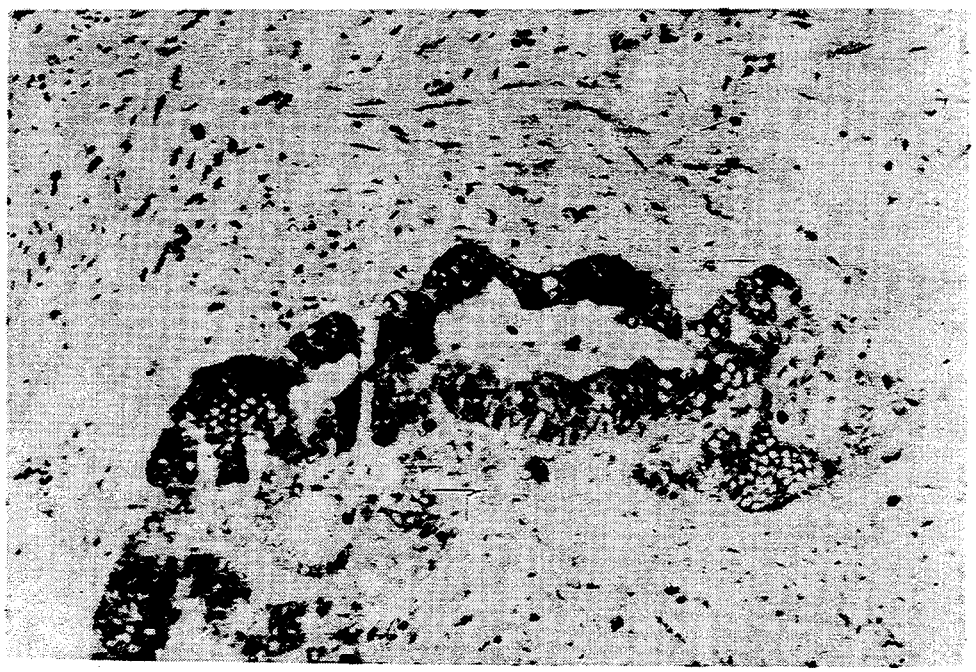
FIGS. 2A and 2B show immunohistochemical staining with C-OU1 of a frozen tissue specimen from colonic adenocarcinoma (2A) and normal tonsillar tissue (2B)
Figure 2B:
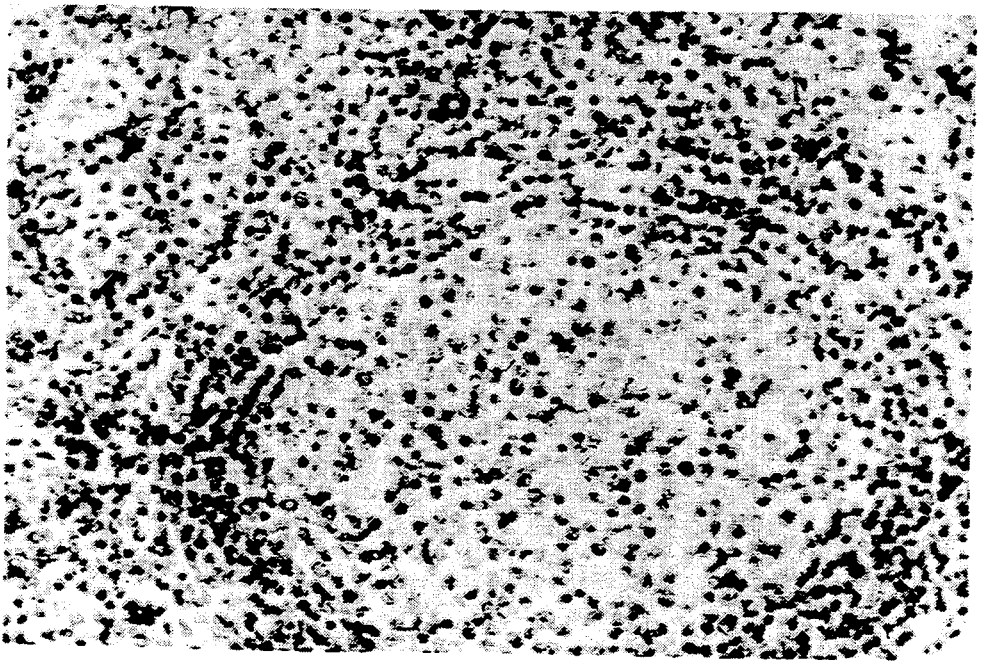

Immunohistochemical analysis was performed on frozen tissue sections fixed in acetone. Endogenous IgM was blocked by incubation with Fab' fragments of anti-µ-chain antibody (purchased from Dakopatts, Copenhagen, Denmark) before the incubation with the hybridoma antibody C-OU1 (0.5 µg/ml) (the Fab' fragments were prepared according to B. Nielsen et al., *Hybridoma* 6 (1), 1987, pp. 103–109) (the hybridoma antibody was concentrated by precipitation with 2M ammonium sulphate). The bound hybridoma antibody was then visualized as described above for the immunocytochemical analysis. In this case the same antibody preparation was labelled with peroxidase as that used for preparing Fab' fragments. FIG. 2A shows than after application of C-OU1, only the tumour cells are stained in a section of a colon adenocarcinoma. FIG. 2B shows the lack of staining Of tonsillar tissue. Table IIA and B summarize the reactivity as analyzed on a variety of tissues, Table IIa showing the results from malignant tissues and Table IIB showing the results from non-malignant tissue.

TABLE IIA

Reactivity of C-OU1 (0.5 µg/ml) on frozen, acetone fixed tissue sections of human malignant tissues analyzed by immunohistochemical techniques

| Tissue | Result |
|---|---|
| Colon adenocarcinoma | 19/21 a) |
| Ovarian adenocarcinoma | 2/2 |
| Renal adenocarcinoma | 1/2 |
| Mammary carcinoma | 7/9 |
| Lung adenocarcinoma | 7/7 |
| Lung epithelial carcinoma | 0/6 |
| Non-seminomal testis carcinoma | 1/1 |
| Sarcoma | 0/3 |
| Malignant melanoma | 0/7 |
| B-lymphoma | 0/1 |
| Thymoma | 0/1 | a) No. positive/No. tested

TABLE IIB

Reactivity of C-OU1 (0.5 µg/ml) on frozen, acetone fixed tissue sections of human normal tissues analyzed by immunohistochemical techniques

| Tissue | Result |
|---|---|
| Ovarian stroma | Negative |
| Ovarian epithelia | Negative |
| Renal glomeruli | Negative |
| Renal tubules | Negative |
| Mammary tubules | Positive |
| Mammary ductuli | Positive |
| Lung alveoles | Negative |
| Bronchial epithelium | Negative |
| Testis | Negative |
| Epidermis | Negative |
| Tonsillary lymhatic tissue | Negative |
| Tonsillary epithelium | Negative |
| Smooth muscles | Negative |
| Blood vessels | Negative |
| Prostate epithelium | Positive |

Normal colon epithelium showed binding of all analyzed human IgM, monoclonal antibodies, myeloma IgM as well as normal polyclonal human IgM. This general binding of IgM to normal colon epithelium was thus judged to be non-specific, an interpretation which was further supported by analysis by electron microscopy and isoelectric focusing (see below). This non-specific binding of antibody is also in accordance with the knowledge of persons skilled in the art.

c) Electron microscopy

For electron microscopy, $10^5$/ml adenocarcinoma cells were cultivated in RPMI-1640 medium, 10% FCS. in tubes with plastic cover slips for 3 days until a monolayer had been obtained. The cells were fixed in 0.1% (v/v) glutaraldehyde in 0.1M PBS. pH 7.2, for 30–60 minutes at 4° C. and then washed in PBS supplemented with bovine serum albumin (BSA) and lysine-HCl overnight at 4° C. The cells were dehydrated in from 30% to 90% ethanol at progressively lower temperatures to −20° C., then infiltrated in Lowicryl K4M (Chemische Werke Lowi, Federal Republic of Germany) at −35° C. and polymerized overnight at −35° C. under ultraviolet light and then for additionally 2 days at ambient temperature.

Ultrathin (50–60 nm) sections of the cell-containing Lowicryl mounted on coated nickel grids were used. The immunomarking procedure consisting in floating the grids with the sections downwards on top of different solutions comprised the following steps: 1) the grids were placed on drops of 1% (w/v) $NaBH_4$ in PBS for 10 minutes; 2) after washing in 0.1% (w/v) BSA-Tris for 2×5 minutes, the grids were transferred to drops of 3% BSA-Tris (15 minutes); 3) the grids were placed on drops of G-OU1 antibody for 1 hour at room temperature; 4) the grids were washed in 0.1% BSA-Tris for 2×5 minutes; 5) the grids were transferred to drops of rabbit anti-human IgM dissolved in 3% BSA-Tris for 1 hour at room temperature; 6) after washing in 0.1% BSA-Tris for 2×5 minutes, the grids were placed on drops of goat anti-rabbit IgG labelled with gold probes (Janssen Pharmaceuticals) of 15 nm, dissolved in 3% BSA-Tris, incubated for 30 minutes at room temperature; 7) the grids were washed in 0.1% BSA-Tris for 2×5 minutes and in redistilled water for 2×5 minutes and dried; and 8) the ultrathin sections were stained with 1% uranyl acetate for 10 minutes and 0.4% lead citrate for 2 minutes at room temperature.

Tween 20 and 0.5M NaCl were added to all antibody and washing solutions.

The ultrathin sections were examined in a JEOL 100-CX electron microscope operating at 80 kV.

Experiments to assess the specificity of the immunocytochemical reactions included omission of the primary antibody and substitution of a human IgM (Cappel) for the primary antibody.

Figure 3A:
FIGS. 3A and 3B show an electron microscopic analysis of the reaction of C-OU1 with Colon 137 cells (colonic adenocarcinoma cells, positive) (3A) and HUTU 80 (duodenal adenocarcinoma cells, negative) (3B)
Figure 3B:

FIG. 3A shows the distinct pattern of the labelling of colon adenocarcinoma cells (Colon 137) in regions around the ends of intermediate filaments and FIG. 3B the lack of labelling (by a similar procedure) of duodenal adenocarcinoma cells (HUTU 80). Sections of colon adenocarcinoma cancer tissue showed labelling only of the tumour cells again associated with intermediate filaments (not shown). Normal colon epithelium showed no labelling. Electron microscopy thus reveals the presence of the target antigen in association with cytoplasmic structures.

d) Isoelectric focusing

Molecular characterization of the target antigen was carried out by isoelectric focusing. Tumour cells or cancer tissue and normal tissue were solubilized by ultrasonication (4×30 seconds on ice) in extraction buffer (75 mM NaCl, 75 mM KCl, 10 mM Hepes, 5 mM EDTA, 5% 2-mercaptoethanol, 5 mg/l Trasylol, 0.01 mM Lenpeptin, 0.01 mM Pepstatin). After ultrasonication, urea was added to 6M together with 80 mg of sucrose and the homogenate was incubated for 30 minutes at 37° C. Insoluble material was removed by centrifugation (5 minutes at 15,000×g).

Isoelectric focusing was performed with the extracts applied onto 1% agarose thin-layer gel (Agarose IEF, Pharmacia) containing 6M urea, 3% (v/v) servalytes 3–10 and 1% (w/v) servalytes 4–6 (Serva). As support gel-based film (LKB) was used. Focusing was performed for 1500 V/h before electrophoretic transfer of the proteins onto nitrocellulose. Remaining binding sites were blocked by incubation of the nitrocellulose in 0.1M Tris-HCl, pH 7.5, containing 0.1M NaCl, 2 mM $MgCl_2$ and 0.05% Tween 20. The nitrocellulose was cut into strips, incubated for 2 hours at room temperature with the hybridoma antibody C-OU1 diluted in PBS-Tween to about 200 ng/ml. After washing with PBS-Tween, the nitrocellulose strips were incubated with alkaline phosphatase conjugated $F(ab')_2$-anti IgM antibody (Jackson Immuno-research) followed by substrate (a solution of 5-bromo-4-chloroindoxyl phosphate and nitro blue tetrazolium).

Figure 4:
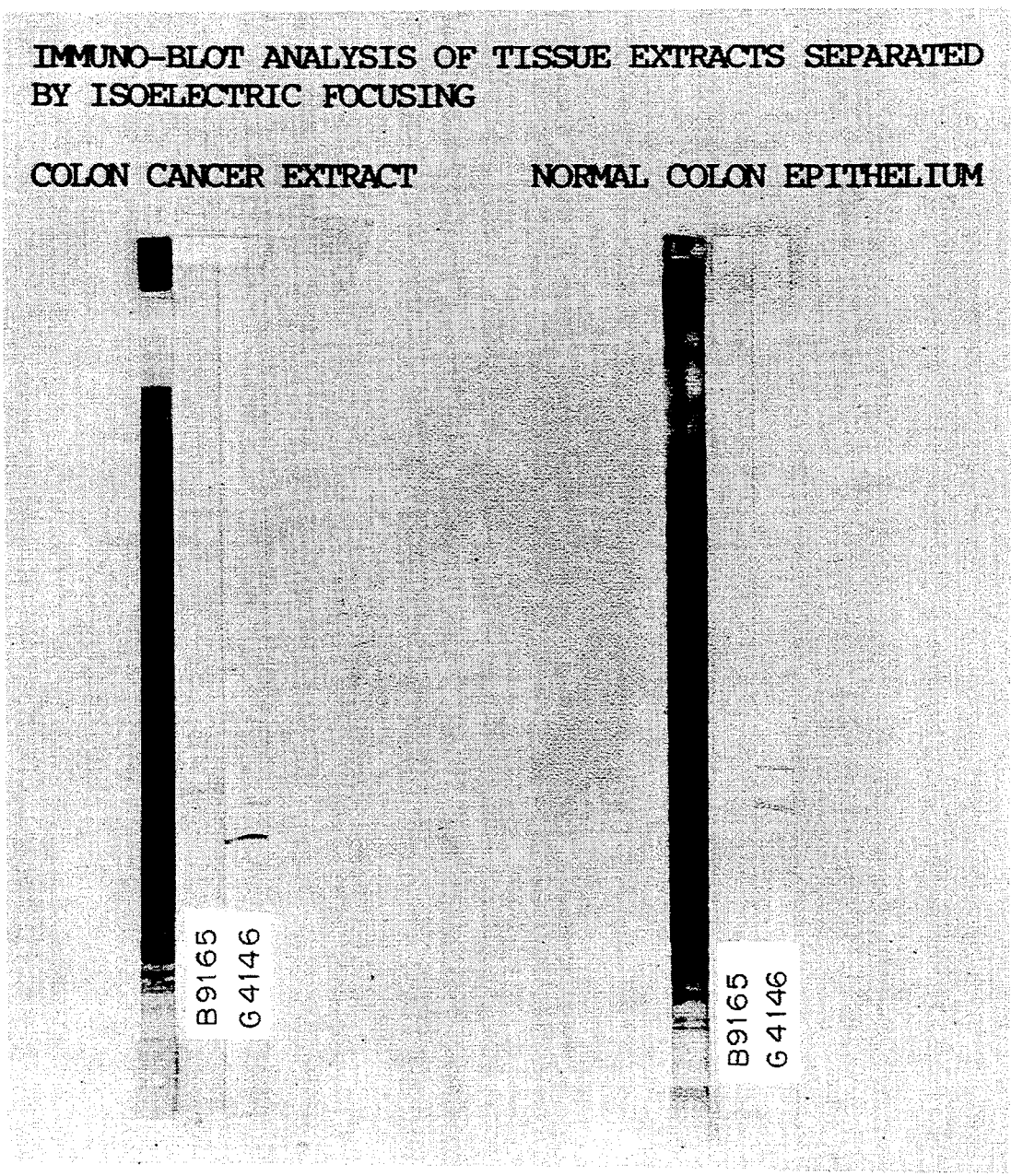
FIG. 4 shows an immuno-blot analysis of tissue extracts separated by isoelectric focusing.

FIG. 4, left panel, shows the staining of extracts of a colon adenocarcinoma tumour and FIG. 4, right panel, an extract of normal colon epithelium. I. staining of total protein with India ink; II. staining with C-OU1; and III. staining with a different hybridoma IgM. Evidently, C-OU1 shows distinct staining of acidic proteins (pI 5.4–6.2) in the tumour extract, but not in the extract of normal colon.

e) SDS-PAGE and Western blotting

Extracts of Colon 137 (colon adenocarcinoma cells) and HUTU 80 (duodenal adenocarctnoma cells) were prepared by solubilization with detergents (2% SDS, 4M urea, 10 mM iodoacetamide) and incubated for 15 minutes before PAGE on 5 to 20% gradient gels. The proteins were then electrophoretically transferred to nitrocellulose sheets. The nitrocellulose sheets were cut into 3 mm strips and incubated overnight at 4° C. with C-OU1 followed by incubation for 2 hours with AP-rabbit anti-human IgM (Sigma). The blots were washed in PBS and fixed by incubation for 15 minutes with 0.2% glutaraldehyde in PBS. Alkaline phosphatase was visualized by incubation for 1 hour at 37° C. with substrate, nitro blue tetrazolium and 5-bromo-4-chloroindoxyl phosphatase. The molecular weight was calculated from the mobility of the following prestained molecular weight markers: $\beta$-galactosidase (116K), fructose-6-phosphatase kinase (84K), pyruvate kinase (58K), fumarase (48.5K), lactic dehydrogenase (36.5K), triosephosphatase isonerase (26.6K).

Figure 5:
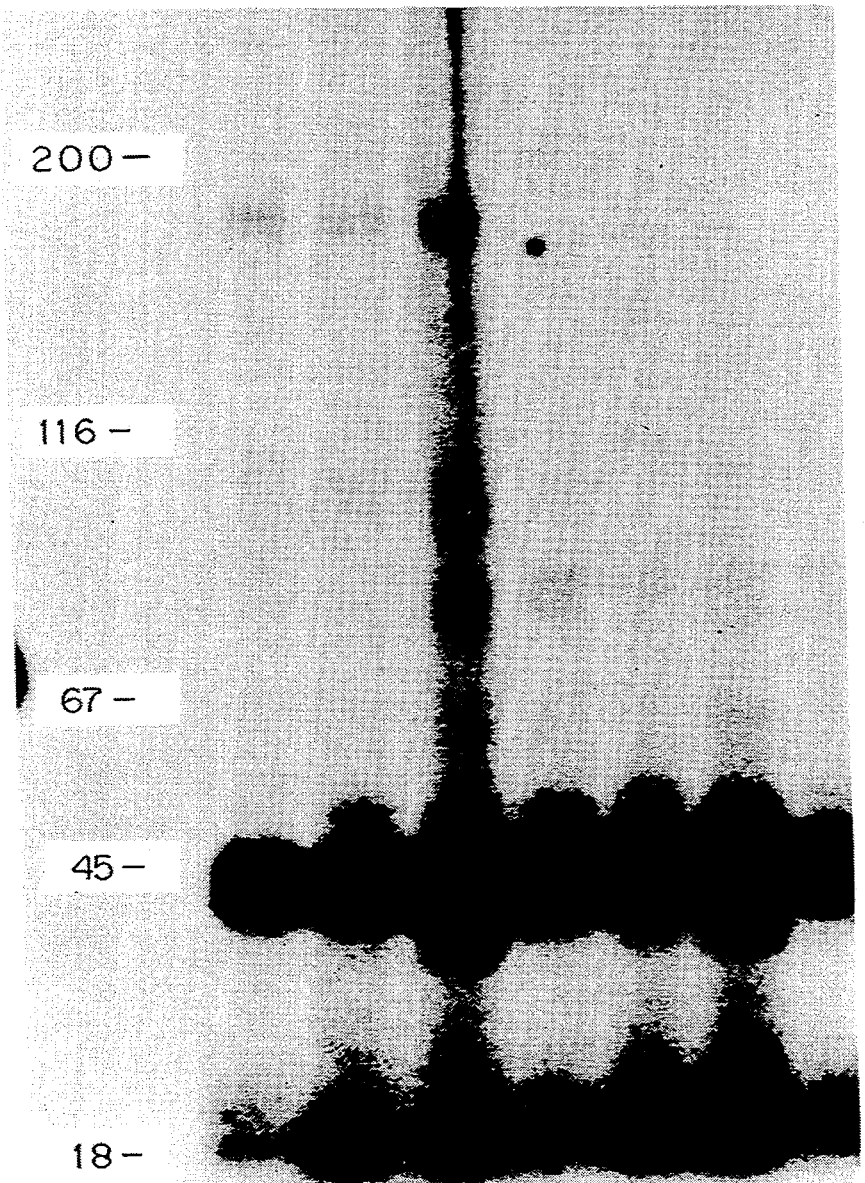
FIG. 5 shows an analysis of carcinoma antigen by SDS-PAGE blotting by labelling with C-OU1. Extract of Colon 137 (colon adenocarcinoma cells, positive) (5A) and extract of HUTU 80 (duodenal adenocarcinoma cells, negative (5B).

The results in FIG. 5 show that C-OU1 reacts with a protein with a molecular weight of 43,000 found in the extracts of colon adenocarcinoma and not in extracts of duodenal adenocarcinoma.

We claim:

1. Monoclonal antibody C-OU1 produced by the human-human hybridoma cell line B9165 (ECACC 87040201).

2. Monoclonal antibody C-OU1, produced by the human-human hybridoma cell line B9165 (ECACC 87040201), or a different monoclonal antibody which specifically, binds the same epitope as is specifically bound by C-OU1, or a specific binding fragment of monoclonal antibody C-OU1 or of said different monoclonal antibody.

3. A specific binding fragment of the antibody of claim 2.

4. The monoclonal antibody or antibody fragment of claim 2 wherein the antibody is produced by a human-human hybridoma cell line.

5. A method of screening a sample of a body fluid or tissue for the presence of a carcinoma-associated antigen which comprises contacting a sample of a body fluid or tissue with the antibody or antibody fragment of claim 2 and detecting the binding of said antibody or antibody fragment to antigen present in the sample.

6. The method of claim 5 in which the antibody or antibody fragment is coupled to an agglutinable particle and binding is detected though agglutination of the particles.

7. The method of claim 5 in which the antibody or antibody fragment is provided with a detectable label.

8. The method of claim 5 in which a second antibody or antibody fragment according to claim 2 is also contacted with the sample, the second antibody or antibody fragment being coupled to a solid support.

9. The method of claim 7 in which the antibody is C-OU1.

10. The method of claim 5 wherein the carcinoma is a colon adenocarcinoma, ovarian adenocarcinoma, renal adenocarcinoma, mammary adenocarcinoma, non-seminomaltestis carcinoma or lung adenocarcinoma.

11. The method of claim 5 wherein the bound carcinoma antigen has a apparent molecular weight of about 43 kD and an isoelectric point in the range of about 5.4–6.2.

12. The method of claim 5 wherein the sample is a tissue sample and the histochemical distribution of the antigen across the tissue sample is evaluated.

13. An intact antibody according to claim 2.

* * * * *